US007473411B2

(12) United States Patent
Ajayan et al.

(10) Patent No.: US 7,473,411 B2
(45) Date of Patent: Jan. 6, 2009

(54) CARBON NANOTUBE FOAM AND METHOD OF MAKING AND USING THEREOF

(75) Inventors: Pulickel Ajayan, Clifton Park, NY (US); Alvaro Carrillo, Troy, NY (US); Nirupama Chakrapani, Troy, NY (US); Ravi S. Kane, Niskayuna, NY (US); Bingqing Wei, Baton Rouge, LA (US)

(73) Assignee: Rensselaer Polytechnic Institute, Troy, NY (US)

( * ) Notice: Subject to any disclaimer, the term of this patent is extended or adjusted under 35 U.S.C. 154(b) by 555 days.

(21) Appl. No.: 11/005,474

(22) Filed: Dec. 7, 2004

(65) Prior Publication Data

US 2006/0073089 A1 Apr. 6, 2006

Related U.S. Application Data

(60) Provisional application No. 60/528,709, filed on Dec. 12, 2003.

(51) Int. Cl.
*D01F 9/12* (2006.01)

(52) U.S. Cl. .................... 423/447.1; 977/742; 428/220; 428/605

(58) Field of Classification Search ............. 423/447.1, 423/447.7; 977/742, 743, 750, 842
See application file for complete search history.

(56) References Cited

U.S. PATENT DOCUMENTS 6,495,258 B1 * 12/2002 Chen et al. .................. 428/408
7,118,693 B2 * 10/2006 Glatkowski et al. ......... 252/502

OTHER PUBLICATIONS

Zhou, et al., Hydrous manganese oxide/carbon nanotube composite electrodes for electrochemical capacitors, J. Solid State Electrochem 2004: 8: 482-487.*

Chakrapani et al., "Capillarity-Induced FormatiOn of Cellular Carbon Nanotube Foams," Power Point Presentation, 14 pages, (Presented at MRS Fall Meeting, Dec. 1, 2003).*

Chakrapani et al., "Capillarity-Induced Formation of Cellular Carbon Nanotube Foams," Power Point Presentation, 14 pages (Presented at the AICHE Annual Meeting, Nov. 17, 2003, San Francisco, California.*

Wang, et al., Honeycomb-like alignments of carbon nanotubes synthesized by pyrolysis of a metal phalocyanine, Applied Physics A: 2000; 71: 347-348.*

Cao, et al., Super-Compressible Foamlike Carbon Nanotube Films, Science 2005; 310: 1307-1310.*

Ajayan, P. M., "Nanotubes From Carbon," Chem. Rev., vol. 99, No. 7, pp. 1787-1799, (1999).

Bowden, N. et al., "Spontaneous Formation of Ordered Structures in Thin Films of Metals Supported on an Elastomeric Polymer," Nature, vol. 393, pp. 146-149, (1998).

(Continued)

*Primary Examiner*—Stuart L. Hendrickson
*Assistant Examiner*—Daniel C. McCracken
(74) *Attorney, Agent, or Firm*—Foley & Lardner LLP

(57) ABSTRACT

A method of making a carbon nanotube structure includes providing an array of substantially aligned carbon nanotubes, wetting the array with a liquid, and evaporating the liquid to form the carbon nanotube structure having a pattern in the carbon nanotube array. The structure is preferably a carbon nanotube foam.

46 Claims, 7 Drawing Sheets a b c d

OTHER PUBLICATIONS

Colina et al., "Experimental Model of Cracking Induced by Drying Shrinkage," Eur. Phys. J., E 1, pp. 189-194, (2000).
Deegan et al., "Capillary Flow as the Cause of Ring Stains from Dried Liquid Drops," Nature, vol. 389, pp. 827-829, (1997).
Drotar et al., "Reflection High-Energy Electron Diffraction from Carbon Nanotubes," Phys. Rev. B 64, 125417, (2001).
Falvo et al., "Bending and Buckling of Carbon Nanotubes Under Large Strain," Nature, vol. 389, pp. 582-584, (1997).
Gelbart et al., "Array Formation in Nanocolloids: Theory and Experiment in 2D," Faraday Discuss., vol. 112, pp. 299-307, (1999).
Gibson, L. J., "Cellular Solids," MRS Bulletin 4, pp. 270-271, (2003).
Girifalco et al., "Carbon Nanotubes, Buckyballs, Ropes, and a Universal Graphitic Potential," Phys. Rev. B 62, pp. 13104-13110, (2000).
Jincao et al., "Prevention of Photoresist Pattern Collapse by Using Liquid Carbon Dioxide," Ind. Eng. Chem. Res., vol. 40, pp. 5858-5860, (2001).
Kessler et al., "Self-Organization of Sorted Patterned Ground," Science, vol. 299, pp. 380-383, (2003).
Kitsunezaki, S., "Fracture Patterns Induced by Desiccation in a Thin Layer," Phys. Rev. E 60, pp. 6449-6464, (1999).
Korneta et al., "On The Classification of Random Two-Dimensional Cellular Structures," Philosophical Magazine Letters, vol. 81, pp. 367-373, (2001).
Lecocq et al., "Experimental Study of Cracking Induced by Desiccation in 1-Dimensional Systems," Ear, Phys. J E 8, pp. 445-452, (2002).
Leung et al., "Pattern Formation—Spiral Cracks Without Twisting," Nature, vol. 410, pp. 166-167, (2001).
Moriarty et al., "Nanostructured Cellular Networks," Physical Review Letters, vol. 89, 248303-1, (2002).
Namatsu et al., "Dimensional Limitations of Silicon Nanolines Resulting from Pattern Distortion Due to Surface Tension of Rinse Water," Appl. Phys. Lett 66, pp. 2655-2657, (1995).
Poncharal et al., "Electrostatic Deflections and Electromechanical Resonances of Carbon Nanotubes," Science, vol. 283, pp. 1513-1516, (1999).
Scherer, G. W., "Theory of Drying," J Ain. Ceram. Soc, vol. 73, pp. 3-14, (1990).
Shorlin et al., "Development and Geometry of Isotropic and Directional Shrinkage-Crack Patterns," Phys. Rev. E 61, pp. 6950-6957 (2000).
Skjeltorp et al., "Fracture in Microsphere Monolayers Studied by Experiment and Computer Simulation," Nature, vol. 335, pp. 424-426, (1988).
Stowell et al., "Self-Assembled Honeycomb Networks of Gold Nanocrystals," Nano Lett., vol. 1, pp. 595-600, (2001).
Tanaka et al., "Freeze-Drying Process to Avoid Resist Pattern Collapse," Jpn. J. Appl. Phys., vol. 32, pp. 5813-5814, (1993).
Thiele et al., "Dewetting of an Evaporating Thin Liquid Film: Heterogeneous Nucleation and Surface Instability," Phys. Rev. Lett., vol. 80, pp. 2869-2872, (1998).
Weaire et al., "Soap, Cells, and Statistics—Random Patterns in 2 Dimensions," Contemporary Physics, vol. 25, pp. 59-99, (1984).
Wei et al., "Assembly of Highly Organized Carbon Nanotube Architectures by Chemical Vapor Deposition," Chem, Mater., vol. 15, pp. 1598-1606, (2003).
Wei et al., "Organized Assembly of Carbon Nanotubes," Nature, vol. 416, pp. 495-496, (2002).
Wong et al., "Nanabeam Mechanics: Elasticity, Strength, and Toughness of Nanorods and Nanotubes," Science, vol. 277, pp. 1971-1975, (1997).
Yuse et al., "Transition Between Crack Pattern," Nature, vol. 362, pp. 329-331, (1993).
Chakrapani et al., "Capillarity Driven Assembly of Two-Dimensional Cellular Carbon Nanotube Foams," Proceedings of the National Academy of Sciences, 101, 4009 (2004).
Hyeok An et al., "Electrochemical Properties of High-Power Supercapacitors Using Single-Walled Carbon Nanotube Electrodes," Advanced Functional Materials, vol. 11, No. 5, pp. 387-392, (2001).
Journal of Metastable and Nanocrystalline Materials: e-vol. 2002, Li Storage Properties of Carbon Nanotubes, http://www.scientific.net/0-87849-497-9/18.htm, pp. 1-3 (2003).
Chakrapani et al., "Formation of Two-Dimensional Cellular Foams From Carbon Nanotube Arrays," Abstract, MRS Fall 2003 Meeting Proceedings, Dec. 1, 2003.

* cited by examiner

Figure 4A
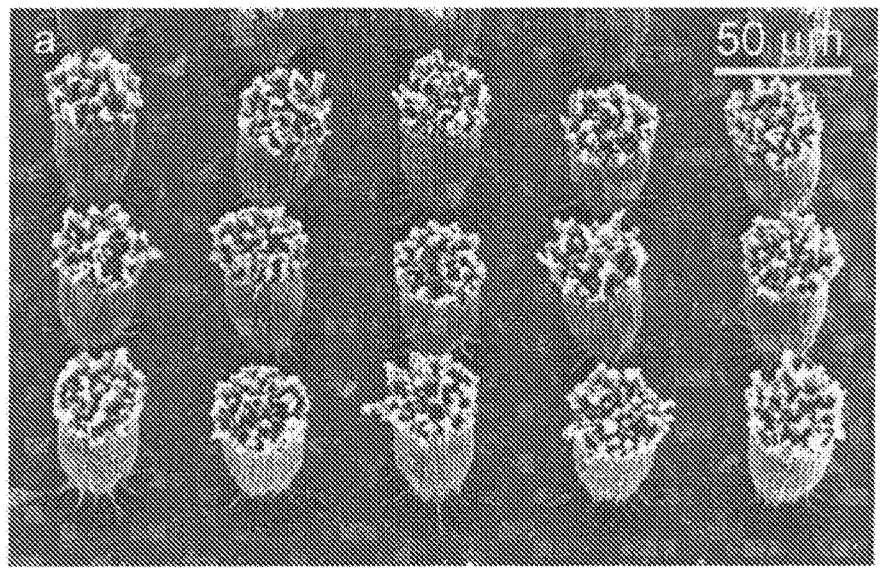
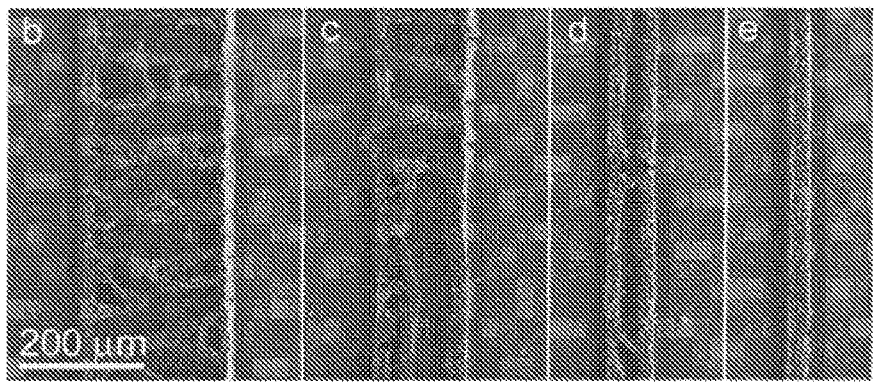
FIGURE 4B FIGURE 4C FIGURE 4D FIGURE 4E

CARBON NANOTUBE FOAM AND METHOD OF MAKING AND USING THEREOF

STATEMENT REGARDING FEDERALLY SPONSORED RESEARCH & DEVELOPMENT

The U.S. government may have certain rights in this invention pursuant to grant number DMR-0408745 from the National Science Foundation and the NSEC.

BACKGROUND OF THE INVENTION

The present invention relates generally to the field of carbon nanotubes and specifically to carbon nanotube foams.

Multi-walled carbon nanotubes (MWNTs) have been produced by several different methods, including chemical vapor deposition (CVD) and laser ablation. These nanotubes are either grown as a layer of aligned nanotubes or as intertwined, randomly oriented bundles of nanotubes.

Carbon nanotubes have many potential applications due to their mechanical, electrical and electronic properties. However, the difficulty in assembling the nanotubes into desired complex architectures and patterns hinder some of these applications.

SUMMARY OF THE INVENTION

One embodiment of the invention relates to a composition of matter comprising of carbon nanotube foam, wherein the nanotubes are extremely compacted.

Another embodiment of the invention relates to a method of making a carbon nanotube structure, comprising of an array of substantially aligned carbon nanotubes, wetting the array with a liquid, and evaporating the liquid to form the carbon nanotube structure having a pattern in the carbon nanotube array.

BRIEF DESCRIPTION OF THE DRAWINGS

FIG. 1A shows a substrate-grown substantially vertically aligned MWNT arrays with an average nanotube diameter of about 30 nm. FIG. 1B is a scanning electron microscopy (SEM) image showing a side-view of cellular structures formed by the evaporation of water from plasma-oxidized substantially vertically aligned MWNTs. The arrow depicts the width of a cell. FIGS. 1C and 1D are higher magnification micrographs showing the cellular structures. The micrograph in FIG. 1D illustrates a "crack" along the floor of a nanotube canyon or depression as well as the bending of nanotubes that gives rise to the open cellular structures. "Bent" nanotubes occupy the floor of the depression in regions surrounding the crack. The inset in FIG. 1D shows the wall of a cell. It can be seen that the alignment of nanotubes has been preserved.

FIG. 2A shows a film composed of substantially vertically aligned carbon nanotubes. FIG. 2B shows the formation of cracks during the evaporation of liquid from the nanotube film. FIG. 2C shows a later stage in the process where the shrinkage of the array and the bending of nanotubes has resulted in the formation of open cellular structures. FIG. 2D is a schematic illustrating the final cellular structure.

FIG. 3A is an optical micrograph during the early stages of structure formation, showing the appearance of cracks. FIGS. 3B and 3C are optical micrographs of the same region at later stages of structure formation. The micrographs demonstrate that cell growth occurs via compaction and bending of the nanotubes. The cell dimensions are governed primarily by the initial crack length and spacing. False coloring has been used for clarity.

FIGS. 4A, 4B, 4C, 4D, 4E, 4F and 4G are SEM images of nanotube patterns where control of structure shape and orientation is accomplished using patterned carbon nanotube films according to the embodiments of the present invention. FIGS. 4A and 4G show wine-glass structures obtained by the evaporation of liquids from cylindrical MWNT arrays. FIGS. 4B-4E show the formation of directional cells in patterned nanotube films. FIG. 4F shows the formation of a two-dimensional carbon nanotube foam by the drying of a patterned MWNT array. The inset in FIG. 4F is a schematic illustrating the formation of the foam from a patterned array, consisting of spatially periodic circular holes, 100 microns in diameter. The structure can be separated from the substrate forming a monolithic carbon nanotube foam.

DETAILED DESCRIPTION OF THE PREFERRED EMBODIMENTS

In a first preferred embodiment, the present inventors have discovered that the carbon nanotubes may be formed into a foam by evaporation of a liquid from nanotubes. As used herein, a nanotube foam comprises a material having a cellular structure. The carbon nanotubes self assemble into the cellular structure pattern due the step of evaporating the liquid from the nanotubes.

Preferably but not necessarily, the carbon nanotube foam comprises of a cellular film containing an open cellular structure. In other words, the foam preferably comprises a "two-dimensional", open celled foam film whose height or thickness in the third dimension is less than, but determined by the height of the initially formed carbon nanotubes. Of course, if desired, plural "two-dimensional" foams may be stacked on top of each other to form a "three-dimensional" structure.

Figures 1A, 1B:
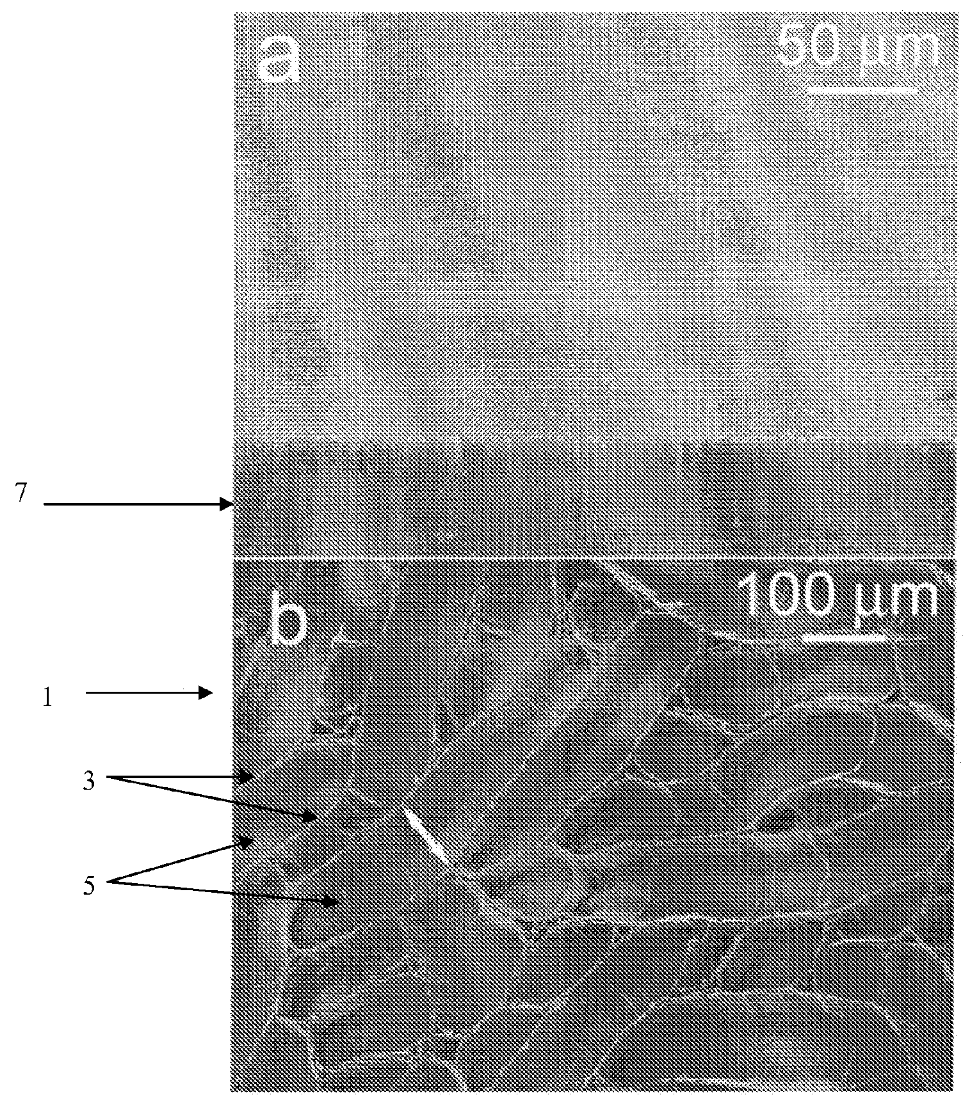
FIGS. 1A, 1B, 1C and 1D are SEM images of nanotube patterns according to the embodiments of the present invention.
Figures 1C, 1D:
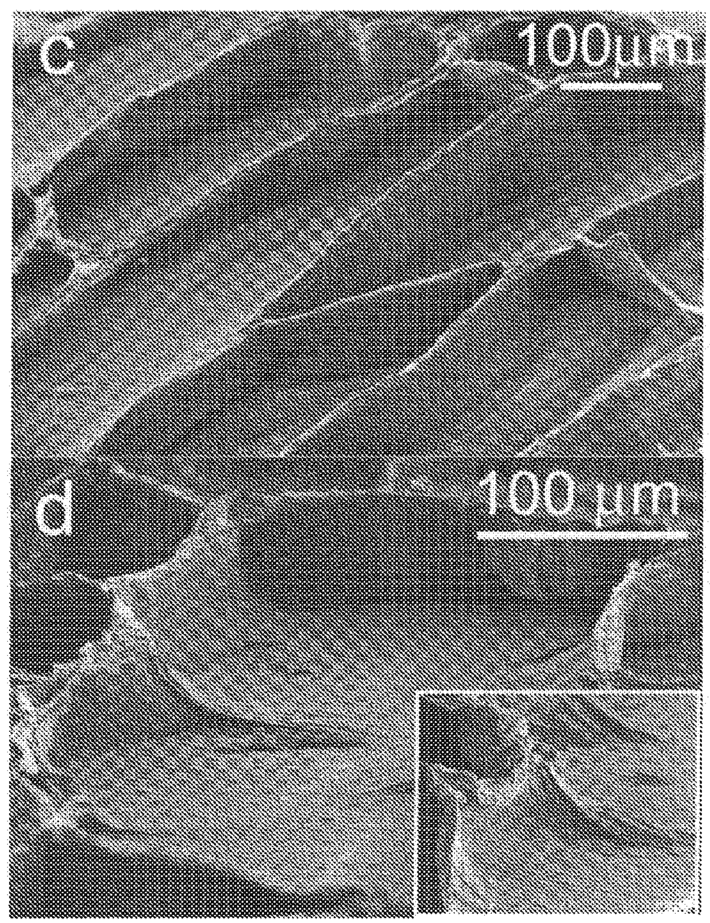

FIGS. 1B-1D show exemplary formation of cellular patterns by the evaporation of liquids from substantially vertically aligned carbon nanotube film shown in FIG. 1A. In a preferred embodiment of the present invention shown in FIG. 1B, the cellular structure of the cellular film 1 comprises a plurality of rims or borders 3 with depressions or canyons 5 located between the rims. Thus, each open cell comprises a depression surrounded by a rim. Adjacent depressions or cells are separated by a common rim or border. The rims and depressions are preferably, but not necessarily, elongated in random or common directions, as shown in FIG. 1B. Preferably, the depressions are elongated in the direction of the elongation of the rims.

The rims comprise of compacted carbon nanotubes substantially aligned in the original or first direction. The depressions comprise carbon nanotubes substantially aligned in a direction substantially perpendicular to the rim elongation direction and substantially perpendicular to the first direction. In other words, when the cellular foam film 1 is oriented horizontally as shown in FIG. 1B, the carbon nanotubes in the rims are substantially aligned in a substantially vertical direction and the carbon nanotubes in the depressions are substantially aligned in a substantially horizontal direction.

The term "substantially aligned" means that at least 50%, preferably at least 75%, most preferably at least 90% of the carbon nanotubes in a particular structure, such as a rim or depression, are aligned in the same direction. For example, as shown in FIGS. 1C and 1D, while the majority of the carbon nanotubes in each rim and depression are oriented in the same direction (i.e., vertical or horizontal), some nanotubes deviate from the common orientation. The terms "substantially vertical" and "substantially horizontal" mean a primary direction that is vertical or horizontal. However, as shown in FIGS. 1C and 1D, some rims are not exactly vertical, but are inclined by less than 20 degrees, such as less than 10 degrees from the vertical direction. Likewise, some depressions are not exactly horizontal, but are inclined by less than 20 degrees, such as less than 10 degrees from the horizontal direction. Furthermore, portions of the rims and depressions are curved, and deviate from the vertical and horizontal directions, respectively. For example, the bottom portions of the rims adjacent to the depressions are sloped from the substantially vertical direction of the middle portions of the rims, while the top portions of the rims are bent away from the substantially vertical direction of the middle portions of the rims. Likewise, edge portions of the depressions adjacent to the rims are sloped upwards from the substantially horizontal direction of the middle portions of the depressions, as shown in FIG. 1D.

The carbon nanotubes in the foam are preferably but not necessarily separated from adjacent carbon nanotubes by less than 10 nm, such as a few nanometers. The rim width depends on the initial density of nanotube array and cell width depends on the initial height of the nanotubes. The rim width can be varied by changing the density of the array. Thus, the foam rims and depressions may have any suitable dimensions. The following exemplary dimensions should not be considered limiting on the scope of the invention. Preferably, but not necessarily, a majority, and preferably at least 75% of the rims have an average length of 50 to 2000 microns and an average width of less than 5 microns. Preferably, but not necessarily, a majority, and preferably at least 75% of the depressions have an average length of 50 to 2000 microns and an average width of 30 to 300 microns.

The carbon nanotubes in the foam preferably comprise multi-walled carbon nanotubes The films comprise of multi-walled carbon nanotubes grown by chemical vapor deposition of ferrocene and xylene.

The preferred method of making carbon nanotube structures comprises providing an array of substantially aligned carbon nanotubes, wetting the array with a liquid, and evaporating the liquid to form the carbon nanotube structure having a pattern in the carbon nanotube array. Without wishing to be bound by a particular theory, the present inventors believe that shrinkage and crack formation in the films due to strong capillary forces during evaporation, and strong van der Waals interactions between condensed nanotubes, result in the formation of visually striking stable cellular patterns and contiguous foams. Patterns formed by nanotube aggregates differ significantly from other polygonal crack patterns, due to the inherent dimensions, strength, and flexibility of the nanotubes. The monolithic nanotube foams assembled on substrates can be elastically deformed and manipulated, transferred to other substrates, and floated out to produce unique freestanding structures.

The step of providing the array of substantially aligned carbon nanotubes preferably comprises growing a film 7 of multi-walled carbon nanotubes on a surface of a substrate by in a direction substantially normal to the substrate surface, as shown in FIG. 1A. For example, substantially vertically aligned multi-walled nanotube arrays are grown on rigid silica substrates using a chemical vapor deposition (CVD) process, as shown in FIG. 1A. The CVD method that delivers the nanotube-forming carbon source and the catalyst material (in compound or elemental form) from the gas phase either simultaneously or sequentially.

For example, CVD nanotube growth can be stimulated by exposing the substrate to vapor mixtures comprising xylenes ($C_8H_{10}$), a nanotube-forming precursor, and ferrocene ($Fe(C_5H_5)_2$), a nanotube catalyst, at about 600 to 1100° C., preferably at about 800 to 900° C. However, other suitable substrates, source gases and temperatures may be used instead. For example, silicon dioxide, silicon oxynitride, magnesium oxide, aluminum oxide or indium tin oxide substrates or layers over any suitable substrates may be used to grow the nanotube films. Ferrocene may be dissolved in xylenes (which preferably contains different isomers) at concentrations of about 0.01 g/ml, the mixture pre-heated, co-evaporated and fed into the CVD chamber. Ferrocene preferably comprises 0.001 to 1 percent of the ferrocene/xylenes mixture. Prolonged growth in the temperature range of 600-1100° C., produces films of densely packed multi-walled carbon nanotubes on the substrate. Uniform, substantially vertically aligned nanotube films having a thickness of a few microns to several tens of microns to several hundreds of microns can be produced in few minutes. The nanotubes in the nanotube films can be about 30 nm diameter multi-walled carbon nanotubes. The films are preferably oxidized in an oxygen plasma to remove any surface carbon impurities and make the surface hydrophilic, though this step is not essential for foam formation. Alternatively, organic solvents may be optionally used instead of the plasma oxidation. Characterization of the oxidized MWNTs by Raman spectroscopy confirms the preservation of their structural integrity.

The oxidized MWNTs may be wetted by a number of liquids, including water. The liquid may comprise a single liquid or a mixture, solution or suspension of liquids. The evaporation of liquids, such as water, from the interstices of the ordered nanotubes in the films produces remarkable results. FIGS. 1B, 1C and 1D show the resulting foam-like structure produced by the reassembly of nanotubes in the films during the drying process. Similar structures can be formed with a variety of liquids including acetone, toluene, dimethylformahide, tetrahydrofuran, and methanol.

The cellular structures are stable once formed, despite the significant deformation of the constituent elastic nanotubes. Preferably, the patterns of cellular structures are not affected by annealing the sample in vacuum at 800° C. for one hour, or by submersion in water followed by another round of evaporation. The nanotube foams, once assembled, are quite elastic and individual cells are elastically deformable. The foams can also be floated out of the substrate, transferred to any other substrate, and are mechanically stable.

To further probe the role of the solvent in pattern formation, the present inventors freeze-dried the wet nanotube films. No cellular structures were observed in the freeze-dried arrays, indicating that pattern formation is formed by evaporation of a liquid from the MWNT arrays.

Figure 2:
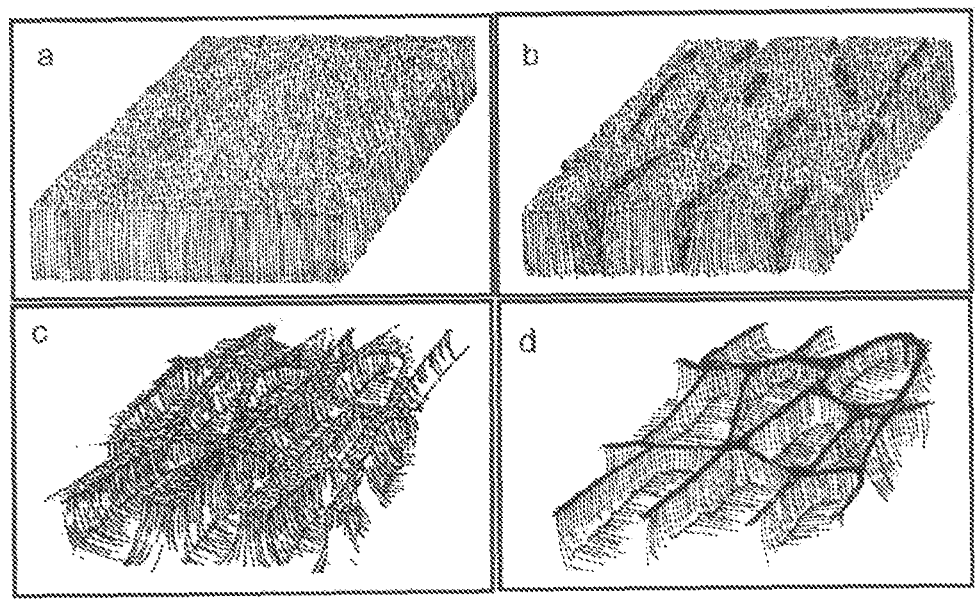
FIGS. 2A, 2B, 2C and 2D are schematic illustrations of the evolution of formation of cellular structures in carbon nanotube films according to the embodiments of the present invention.
Figures 3A, 3B, 3C:
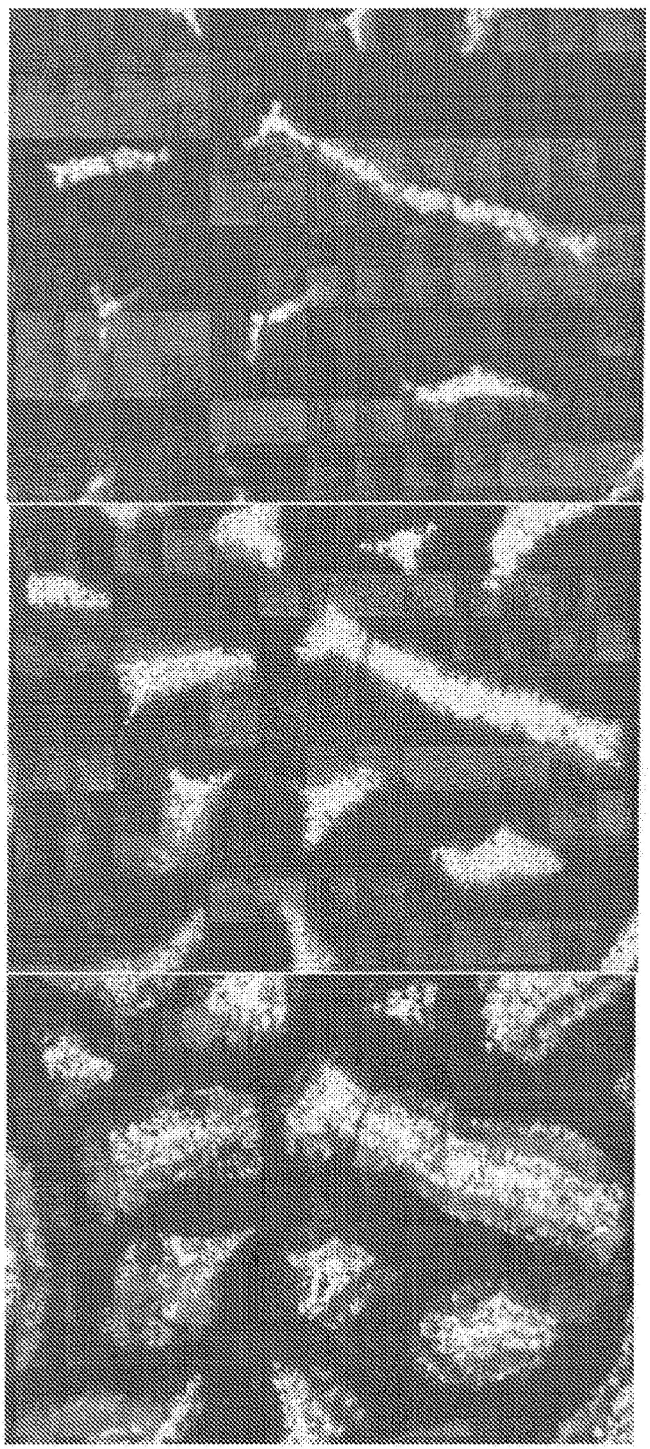
FIGS. 3A, 3B and 3C are optical micrographs illustrating the morphological evolution over time of cellular structures during the evaporation of water from a carbon nanotube film according to the embodiments of the present invention.

The real-time collapse and collective morphological evolution of the nanotubes into cellular structures is shown using schematics in FIGS. 2A-2D and optical microscope micrographs in FIGS. 3A-3C. These Figures illustrate the macroscale features that develop and change in the films. These Figures illustrate that drying-induced micro-crack formation, and further in-plane shrinkage of the nanotube arrays accompanied by the bending of nanotubes, results in the formation of the observed cellular structures. While mechanisms based on Marangoni convection and the nucleation and growth of holes have been proposed to explain the formation of cellular networks in dried nanoparticle suspensions, the elongated polygonal structures seen in FIGS. 1 and 3 are probably incompatible with these mechanisms, which would be expected to give rise to regular polygonal networks. In addition, the substrate-grown nanotubes do not convect, as required for pattern formation by Marangoni convection.

The open cellular structures formed by MWNT arrays are significantly different from other polygonal crack patterns, such as the shrinkage crack patterns in mud, clay, and cement, and columnar joints formed in cooling basaltic lavas. Unlike systems in which cracks tend to propagate until stopped by other pre-existing cracks, crack propagation in the MWNT arrays is usually arrested before cracks meet, as shown in FIG. 3A. Consequently, these structures comprise a polygonal network of compacted MWNT rims surrounding discrete depressions, instead of a polygonal network of cracks. These cellular structures do not evolve via cell division or coalescence. While image analysis reveals that the average crack length is greater than the average cell width, the growth of an individual crack takes places on a time scale of seconds, whereas the subsequent shrinkage and bending of nanotubes (FIGS. 3B and 3C) is much slower, and takes place on a time scale of minutes.

Without wishing to be bound by a particular theory, the present inventors believe that the formation of open cellular structures by the collapse (bending) and reassembly (mainly condensation) of nanotubes shown in FIGS. 1-3 is a result of the remarkable mechanical and structural properties of the MWNTs, including their alignment, narrow spacing, high aspect ratios, flexibility, and mechanical strength. While the evaporative flux during the drying of the nanotube film tends to reduce the height of liquid in the film, the bending of the nanotubes ensures that the liquid/vapor interface remains at the surface of the film. Without wishing to be bound by a particular theory, the present inventors believe that the narrow spacing between the MWNTs (on the order of tens of nanometers, such as less than 75 nanometers, for example) results in large surface tension-induced differences between the pressures of air and solvent. Assuming that MWNTs have an average spacing of 50 nm, it is estimated the initial pressure difference to be 6 MPa. The pressure difference is inversely proportional to the spacing between the nanotubes, and increases in magnitude during the consolidation of the nanotube film. The pressure difference exerts a bending moment on the nanotubes.

Without wishing to be bound by a particular theory, the present inventors believe that the high aspect ratio of the MWNT enhances the magnitude of the pressure-induced deflection. The maximum deflection ($\delta$) of a beam due to a uniformly distributed load can be expressed as $\delta = WL^3/8EI$, where $W(=PDL)$ is the total force, L is the length, D is the diameter, E is the bending modulus, P is the pressure difference, and $I (=\pi D^4/64)$ is a cross-sectional second moment. Estimates of the value of the bending modulus for MWNTs, 30 nm in diameter, range from 0.1-1.28 TPa. Assuming a value of 1 TPa for the bending modulus of a MWNT, which is similar to the value of the modulus along the basal plane of highly oriented pyrolytic graphite, it is estimated that a pressure difference of only 1.1 Pa is sufficient to cause a maximum deflection of 10 μm for an MWNT that is 30 nm in diameter and 100 μm long. Assuming that the value of the bending modulus remains relatively constant, a pressure difference of only 5.5 kPa would be sufficient to cause a maximum deflection of about 50 μm for each nanotube in a linear array consisting of a thousand MWNTs. Capillary forces are therefore large enough to cause the bending of the MWNTs seen in FIGS. 1B-1D. It is believed that these large deformations are possible on account of the extraordinary flexibility of the MWNTs and their resistance to fracture.

Without wishing to be bound by a particular theory, the present inventors believe that while the deformation of nanotubes and the resulting formation of open cells can be attributed to the magnitude of the capillary forces, FIG. 1B also suggests that there is a length scale associated with these cellular structures. Real space image analysis reveals that the distribution of cell widths in the cellular structures is narrower than the distribution of crack lengths. The average cell width varies linearly with the length of the nanotubes in the array (i.e. with the height of the nanotube film). Without wishing to be bound by a particular theory, the present inventors believe that this linearity can be explained by theoretical studies of crack pattern formation using spring-block models. The adhesion between the nanotube film and the substrate hinders the contraction of the film at its base. Inhomogeneous shrinkage results in the accumulation of stress in the film. The length scale associated with the pattern (and hence the average cell width in the MWNT cells) would be expected to vary linearly with the film height if crack formation occurs due to a critical stress criterion. FIGS. 3A-C indicate that the cell width is, to a large extent, governed by the initial pattern of cracks. The length scale associated with the initial crack pattern (FIG. 3A), and the slow and uniform widening of the cracks (FIGS. 3B and 3C), results in the formation of cells having substantially uniform widths.

The present inventors also tested the effect of the rate of evaporation of the solvent (water) on pattern formation by allowing the structures to form under different ambient humidity conditions at room temperature. A lower value of the relative humidity (RH), i.e. a faster rate of evaporation, favors crack formation and results in a decrease in the average cell width. The average cell width increases linearly with increasing relative humidity, in the range of humidity values tested (RH between 50 and 80%). Thus, at least one of a size and a shape of the cellular pattern may be controlled by controlling at least one of the carbon nanotube length, a rate of evaporation of the liquid and a geometry of the carbon nanotube film.

While the results described above illustrate the ability to control the pattern length scale by varying experimental parameters, the use of patterned MWNT arrays provides striking control over the orientation and shape of the structures, as shown in FIGS. 4A-G.

Figure 4F:
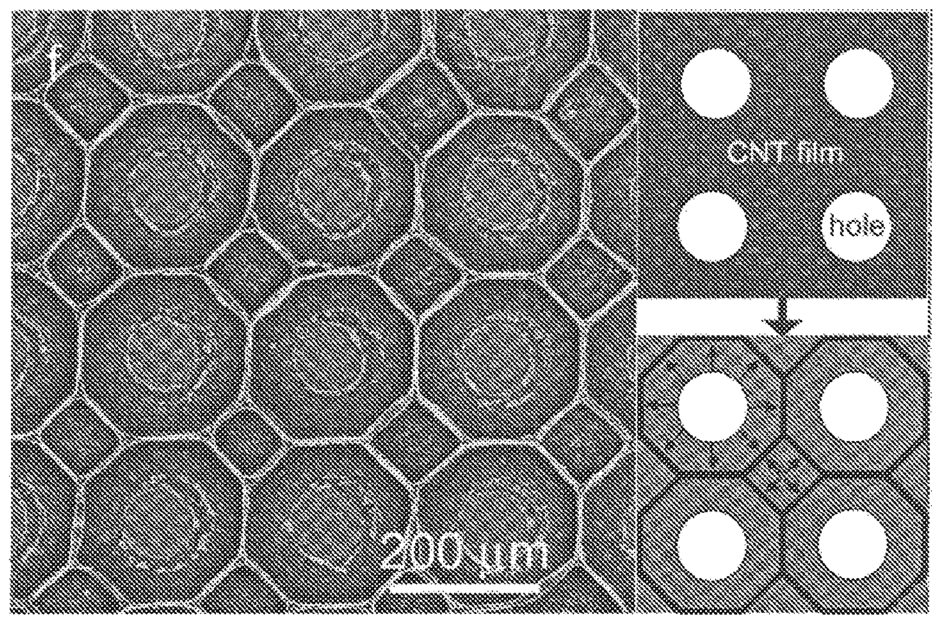
Figure 4G:
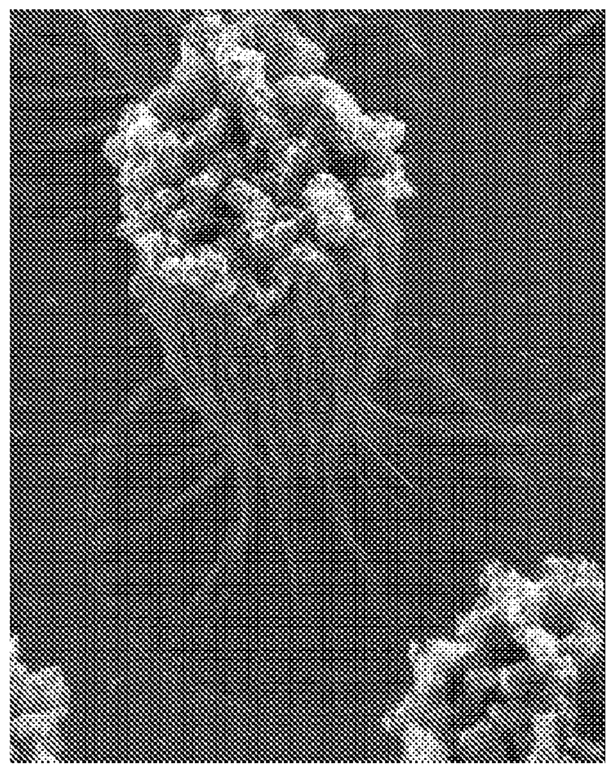

FIGS. 4A and 4G shows structures formed by the evaporation of liquids from spatially periodic cylindrical MWNT arrays. The cylindrical MWNT arrays may be formed by any suitable method. For example, these arrays may be formed by selective CVD growth on circular template material, such as silicon oxide template material on a silicon substrate, as described in United States published application US-2003-0165418-A1, incorporated herein by reference in its entirety or by patterning a monolithic array of nanotubes. After plasma oxidation (and/or organic solvent treatment), wetting with liquid and evaporation of the liquid, the cylindrical MWNT arrays are compacted near their base to a third of their original diameter, forming "wine-glass" structures. This degree of compaction is consistent with MWNTs, initially separated by about 50 nm, coming in close contact. This consolidation, and the strong van der Waals interactions between condensed nanotubes, explains the stability of the cellular structures despite the extensive deformation of the constituent nanotubes.

FIGS. 4B-4E provide another example of the control of structure formation. The samples in FIGS. 4B-4E (consisting of aligned MWNTs having a length of about 60 μm) were plasma oxidized, immersed in acetone, and dried under ambient conditions. Without being bound by a particular theory, the present inventors believe that rectangular MWNT patterns having an aspect ratio (i.e. a ratio of width to height) smaller than a critical value give rise to unidirectional cracks and that the resulting cellular structures would also be directional.

FIG. 4B-4E show cellular structures formed in patterned MWNT arrays located in different regions on the same substrate, and therefore having the same film height. The array width influences the direction of crack growth. The micrographs also reveal the inward bending of the nanotubes due to capillary forces. While wider MWNT arrays show cells oriented in multiple directions, unidirectional cells are seen below a certain width as shown in FIG. 4B. More complex behavior was observed on further decreasing the width of the patterned arrays shown in FIGS. 4C-4E. A transition region, consisting of cells oriented both perpendicular and parallel to the length of the pattern, were seen for arrays having an initial width of 200 μm, as shown in FIG. 4C. For arrays with smaller widths shown in FIG. 4D, cells were unidirectional, but oriented parallel to the length of the pattern, whereas cell formation was not observed in arrays having widths smaller than 100 μm, as shown in FIG. 4E. FIG. 4E reveals a significant compaction of the array due to capillary forces. Inward bending of the nanotubes at the edges of the pattern is also seen in the wider MWNT arrays (FIGS. 4B-4D).

Thus, in FIG. 4B, the cellular nanotube film comprises a film having a predetermined width (i.e., the film width is selected from a first range) such that the elongation direction of the depressions is substantially perpendicular to the film width (i.e., at least 75% of the depressions are elongated perpendicular to the film width). In contrast, in FIG. 4D, the cellular nanotube film comprises a film having a predetermined width (i.e., the film width is selected from a different second range which is less than the first range) such that the elongation direction of the depressions is substantially parallel to the film width (i.e., at least 75% of the depressions are elongated parallel to the film width).

Without being bound by a particular theory, the present inventors believe that this inward bending suppresses crack formation perpendicular to the length of the pattern (FIG. 4D) and parallel to the length of the pattern for the narrower patterns (FIG. 4E). Furthermore, without being bound by a particular theory, the present inventors believe that the actual value of the critical array width to obtain cell directionality varies with different array and process variables, such as nanotube height and spacing, for example.

FIG. 4F shows the formation of a two-dimensional carbon nanotube foam with a predetermined, controlled two dimensional cellular pattern by the drying of a patterned MWNT array. In other words, the pattern of cells may be controlled to have a desired or predetermined shape of each cell and layout of the cells in the pattern rather than a random or uncontrolled cell shape and layout. Each cell may have a polygonal, circular, oval or complex (i.e., non-polygonal, non-circular and non-oval) shape and the cell layout may be ordered and/or geometric (i.e., an ordered pattern of polygonal cells, for example) or disordered, if a disordered pattern is desired.

For example, by selectively growing or patterning nanotubes on a template material having spatially periodic circular holes, 100 microns in diameter (shown in the inset to FIG. 4F) results in a consolidation of the rims during the drying of the patterned MWNT array and results in the formation of a two-dimensional foam consisting of mainly square and octagonal cells. Thus, as shown in FIG. 4F, the cellular structure comprises a plurality of different predetermined cellular patterns (alternating square and octagonal cells arrangements).

The structures shown in FIGS. 4A and 4E are examples of bundles of carbon nanotubes aligned in a same direction (i.e., vertically). In both cases a base of the bundle has a width that is less than a top of the bundle. The top of the bundle is located above the base of the bundle. The base of the bundles is located in contact with a surface of a substrate, such as the CVD template material, which promotes growth of carbon nanotubes in a direction normal to the substrate. The bundle shown in FIG. 4A comprises a circular or oval bundle having a smaller base diameter than a corresponding top diameter. The bundle shown in FIG. 4E comprises a polygonal or a substantially two dimensional (i.e., linear) bundle. Other bundle configurations may be formed depending in the shape of the nanotubes that are subjected to wetting and evaporation.

The cellular films or bundles described above grown on the substrate can be separated from the substrate forming a monolithic, free standing carbon nanotube structure, such as free standing foam or free standing bundles. The free standing structure can then be attached to a different substrate or placed into a desired device. A monolithic freestanding carbon nanotube structure, such a foam is readily obtained by separating the structure from the substrate by immersion into aqueous hydrofluoric acid or other selective etching media which selectively etch away the substrate or etches away a release layer located between the substrate and the nanotube selective growth template layer. Thus, a free standing monolithic carbon nanotube structure which does not require an adhesive substance nor a supporting substrate to maintain the structure shape (i.e., to maintain the nanotubes attached to each other) can be formed. Preferably, this structure comprises MWNTs and has a shape of a sheet, free standing membrane or film. This structure may be placed onto a support or incorporated into a suitable device, such as a filter.

The above described ability to control structure formation in the MWNT arrays and the remarkable properties of the constituent nanotubes provides the ability to produce various carbon nanotube based articles of manufacture, such as devices and materials. The method of making nanotube foams and structures described above can be used in fabrication of macroscopic two-dimensional foams having cells of a variety of shapes, and lateral extent of macro-scale dimensions. The capillarity-induced nanotube consolidation, and the resulting strong inter-tube interaction, can be used for fabricating lightweight carbon nanotube foams having exceptional mechanical properties.

For example, in one embodiment of the invention, the nanotube foam comprises or is incorporated into a composite shock absorbing material, such as a shock-absorbent structural reinforcement. Since the cellular structures are deformable and elastic as well as light-weight, they are attractive for impact energy absorption. If desired, a polymer material may be impregnated into the foam to form the shock-absorbent material. The shock absorbent material may be incorporated into any device or structure which requires shock absorbency, such as a vehicle or an aircraft.

In another embodiment of the invention, the nanotube foam comprises or is incorporated into an acoustic damping material. The acoustic damping material may be incorporated into any suitable device or structure, such as sensitive testing and measuring apparatus.

In another embodiment of the invention, the foams with pre-defined porosities and wall-thickness can be used as elastic membranes and fabrics. In other words, the free standing nanotube film can be used as an elastic membrane for various devices which require such membranes. The nanotube foam can also be sheet shaped and used instead of fabric for clothes, drapes, blankets and other articles incorporating traditional fabrics. Alternatively, the nanotube foam can be incorporated into or attached to at least one side of a traditional fabric as an electrically conductive layer.

In another embodiment of the invention, the carbon nanotube foam is incorporated into a composite material comprising the carbon nanotube foam and a non-carbon nanotube material. The non-carbon nanotube material may be selected from polymer, ceramic, metal and other suitable materials. The composite foam may comprise of non-carbon nanotube material reinforced by the nanotube structure.

In another embodiment of the invention, the carbon nanotube foam is incorporated into a filter. The foam is formed with pores having a size less than 10 nanometers. The filter may comprise a free standing nanotube foam film or the foam film may be placed over other porous material and/or attached to a handle. The filter may be used in a method of filtering any suitable medium, such as a liquid biological medium, which comprises passing the medium through the carbon nanotube foam filter. The foam cell size may be selected to match those of biological cells to use the horizontally aligned nanotubes in the depressions as a cell filter or separator.

In another embodiment of the invention, the nanotube foam may be used as a biological cell growth matrix. In this embodiment, cells are grown in the carbon nanotube foam. In another embodiment of the invention, the nanotube foam may be used as a therapeutic agent matrix. For example, the foam may be used as a matrix which stores any suitable therapeutic agent, such as a gene, protein or molecular pharmaceutical substance, in the depressions of the foam. The therapeutic agent may be any substance that provides a therapeutic effect to treat a condition in a mammal. Thus, the foam may be used as a controlled release matrix from which the therapeutic agent is controllably released over time, such as after the matrix is provided into a body of a mammal (i.e., animal or human). For example, the matrix may be provided orally or via injection to the mammal in need thereof.

In another embodiment of the invention, the carbon nanotube foam is incorporated into an electrochemical storage device electrode. Various electrochemical devices, such as fuel cells, batteries, such as Li-ion batteries and hydrogen storage batteries, and supercapacitors (also known as electrochemical capacitors) contain carbon nanotubes located in a conductive foam, such as foam metals, including nickel foams. The carbon nanotube foam described above may be used as the electrode of the electrochemical device or in combination with another conductive material, such as a nickel sheet, rod or foam as the electrode. If desired, a current collector may also be placed in contact with the electrode.

Furthermore, ceramic and metallic foams are often formed by forming a polymer foam template and then forming a ceramic or metal foam on the template by any suitable process such as dip coating or electrolytic deposition. The carbon nanotube foam may be used as a template for the formation of metal or ceramic foams by dip coating the template with a ceramic precursor slurry or electrolytically depositing a metal onto the template. The template may then be removed or incorporated into a composite nanotube/metal or ceramic foam. The nanotube foam is advantageous compared to the polymer foam because the cell structure and pattern in the nanotube foam may be designed and controlled with a high degree of precision, as described above.

The above described structures also provide an interesting example of the spontaneous generation of complex patterns from highly ordered media. The ability to control the length scale, orientation, and shape of the structures, and the simplicity of the structure-formation process makes this a particularly attractive system for studying pattern formation.

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

What is claimed is:

1. A composition of matter comprising a carbon nanotube foam, wherein the foam comprises a cellular film containing an open cellular structure and the film is located on a substrate which promotes growth of carbon nanotubes in a direction normal to the substrate surface, wherein:

the cellular structure of the cellular film comprises rims and depressions;

the rims comprise carbon nanotubes substantially aligned in a first direction; and the depressions comprise carbon nanotubes substantially aligned in a second direction substantially perpendicular to the first direction.

2. The composition of claim 1, wherein:

the rims comprise elastic elongated rims comprising compacted carbon nanotubes, wherein the first direction is substantially perpendicular to the rim elongation direction; and the depressions are located between the rims, wherein the second direction is substantially perpendicular to the rim elongation direction.

3. The composition of claim 2, wherein the carbon nanotubes in the rims are substantially aligned in a substantially vertical direction and the carbon nanotubes in the depressions are substantially aligned in a substantially horizontal direction when the cellular film is arranged in a horizontal direction.

4. The composition of claim 2, wherein the carbon nanotubes comprise multiwalled carbon nanotubes.

5. The composition of claim 2, wherein:

the open cellular structure comprises a substantially polygonal network of rims enclosing discrete depressions; and a height of the rims is less than, but determined by a height of the carbon nanotubes.

6. The composition of claim 2, wherein the depressions comprise elongated depressions.

7. The composition of claim 6, wherein the depressions are elongated in a direction of elongation of the rims.

8. The composition of claim 7, wherein the cellular film comprises a film having a predetermined width such that the elongation direction of the depressions is substantially parallel to the film width.

9. The composition of claim 7, wherein the cellular film comprises a film having a predetermined width such that the elongation direction of the depressions is substantially perpendicular to the film width.

10. The composition of claim 2, wherein:

a majority of the rims have an average length of 50 to 2000 microns and an average width of less than 5 microns; and a majority of the depressions have an average length of 50 to 2000 microns and an average width of 30 to 300 microns.

11. The composition of claim 1, wherein the rims and depressions form a predetermined, controlled, two dimensional pattern.

12. The composition of claim 1, wherein the carbon nanotubes in the foam are separated from adjacent carbon nanotubes by less than 10 nm.

13. The composition of claim 1, wherein the cellular structure comprises a plurality of different predetermined cellular patterns.

14. The composition of claim 1, wherein the foam comprises an elastically deformable and mechanically stable substantially two dimensional foam.

15. The composition of claim 1, wherein the composition comprises a composite material comprising the carbon nanotube foam and a non-carbon nanotube material.

16. The composition of claim 15, wherein the non-carbon nanotube material is selected from polymer, ceramic and metal materials.

17. A composition of matter comprising a carbon nanotube foam, wherein the carbon nanotube foam comprises a cellular film containing an open cellular structure and the carbon nanotubes in the foam are separated from adjacent carbon nanotubes by less than 10 nm, wherein:

the cellular structure of the cellular film comprises rims and depressions;

the rims comprise carbon nanotubes substantially aligned in a first direction; and the depressions comprise carbon nanotubes substantially aligned in a second direction substantially perpendicular to the first direction.

18. The composition of claim 17, wherein the composition comprises a monolithic free standing carbon nanotube foam.

19. The composition of claim 17, wherein the carbon nanotube foam does not require an adhesive substance nor a supporting substrate to maintain the open cellular structure shape.

20. structure of claim 19, wherein the carbon nanotubes comprise MWNTs.

21. The structure of claim 20, wherein the structure comprises a cellular foam.

22. The structure of claim 21, wherein the structure has a shape of a sheet, a free standing membrane or a film.

23. The structure of claim 22, wherein the structure is located on support or incorporated into a device.

24. A composition of matter comprising a carbon nanotube foam, wherein the carbon nanotube foam comprises a cellular film containing an open cellular structure and the cellular structure of the cellular film comprises:

elastic elongated rims comprising compacted carbon nanotubes substantially aligned in a first direction which is substantially perpendicular to the rim elongation direction; and depressions located between the rims, wherein the depressions comprise carbon nanotubes substantially aligned in a second direction substantially perpendicular to the rim elongation direction and substantially perpendicular to the first direction.

25. The composition of claim 24, wherein the carbon nanotubes in the rims are substantially aligned in a substantially vertical direction and the carbon nanotubes in the depressions are substantially aligned in a substantially horizontal direction when the cellular film is arranged in a horizontal direction.

26. The composition of claim 24, wherein the carbon nanotubes comprise multiwalled carbon nanotubes.

27. The composition of claim 24, wherein:

the open cellular structure comprises a substantially polygonal network of rims enclosing discrete depressions; and a height of the rims is less than, but determined by a height of the carbon nanotubes.

28. The composition of claim 24, wherein the depressions comprise elongated depressions.

29. The composition of claim 28, wherein the depressions are elongated in a direction of elongation of the rims.

30. The composition of claim 29, wherein the cellular film comprises a film having a predetermined width such that the elongation direction of the depressions is substantially parallel to the film width.

31. The composition of claim 29, wherein the cellular film comprises a film having a predetermined width such that the elongation direction of the depressions is substantially perpendicular to the film width.

32. The composition of claim 24, wherein:

a majority of the rims have an average length of 50 to 2000 microns and an average width of less than 5 microns; and a majority of the depressions have an average length of 50 to 2000 microns and an average width of 30 to 300 microns.

33. A composition of matter comprising a carbon nanotube foam, wherein the carbon nanotube foam comprises a cellular film containing an open cellular structure and the cellular structure of the cellular film comprise rims and depressions which form a predetermined, controlled, two dimensional pattern, wherein:

the rims comprise carbon nanotubes substantially aligned in a first direction; and the depressions comprise carbon nanotubes substantially aligned in a second direction substantially perpendicular to the first direction.

34. A composition of matter comprising a carbon nanotube foam, wherein the carbon nanotube foam comprises a cellular film containing an open cellular structure and the cellular structure comprises a plurality of different predetermined cellular patterns, wherein:

the cellular structure of the cellular film comprises rims and depressions;

the rims comprise carbon nanotubes substantially aligned in a first direction; and the depressions comprise carbon nanotubes substantially aligned in a second direction substantially perpendicular to the first direction.

35. A flexible membrane comprising the carbon nanotube foam of claim 1.

36. A filter having pores of less than 10 nanometers comprising the carbon nanotube foam of claim 1.

37. An article of manufacture comprising a shock absorbing material comprising the carbon nanotube foam of claim 1.

38. An article of manufacture comprising an acoustic damping material comprising the carbon nanotube foam of claim 1.

39. A composite material comprising a matrix material and a reinforcing material comprising the carbon nanotube foam of claim 1.

40. A fabric comprising the carbon nanotube foam of claim 1.

41. An electrochemical storage device electrode comprising the carbon nanotube foam of claim 1.

42. A cell growth matrix comprising the carbon nanotube foam of claim 1.

43. A method of growing cells comprising growing cells in the carbon nanotube foam of claim 1.

44. A method of filtering a medium comprising passing the medium through the carbon nanotube foam of claim 1.

45. The method of claim 44, wherein the medium comprises a biological medium.

46. A therapeutic agent delivery system comprising the nanotube foam of claim 1 as a matrix and a therapeutic agent located in the matrix.

* * * * *